United States Patent
Lee et al.

(10) Patent No.: US 7,183,963 B2
(45) Date of Patent: Feb. 27, 2007

(54) SYSTEM AND METHOD FOR INSPECTING TRANSPORTABLE ITEMS USING MICROWAVE IMAGING

(75) Inventors: Gregory Steven Lee, Mountain View, CA (US); Robert C. Taber, Palo Alto, CA (US); Izhak Baharav, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/088,831

(22) Filed: Mar. 24, 2005

(65) Prior Publication Data

US 2006/0214835 A1   Sep. 28, 2006

(51) Int. Cl.
  *G01S 13/88*   (2006.01)
  *G01S 13/89*   (2006.01)
  *G01V 3/12*    (2006.01)
  *G01S 13/00*   (2006.01)
  *G01S 7/40*    (2006.01)

(52) U.S. Cl. .................... 342/22; 342/25 R; 342/25 A; 342/27; 342/59; 342/73; 342/74; 342/81; 342/175; 342/176; 342/179; 342/195

(58) Field of Classification Search .................. 342/21, 342/22, 25 R–25 F, 27, 28, 73–82, 89, 90, 342/165–176, 179, 190–197, 351, 59; 250/336.1, 250/353, 390.04
See application file for complete search history.

(56) References Cited

U.S. PATENT DOCUMENTS

| 4,502,025 | A |   | 2/1985  | Carl, Jr. et al. |
|-----------|---|---|---------|------------------|
| 4,521,861 | A | * | 6/1985  | Logan et al. ................ 342/351 |
| 4,649,393 | A |   | 3/1987  | Rittenbach |
| 4,825,215 | A | * | 4/1989  | Wiley .......................... 342/351 |
| 4,885,592 | A |   | 12/1989 | Kofol et al. |
| 5,027,125 | A |   | 6/1991  | Tang |
| 5,081,456 | A | * | 1/1992  | Michiguchi et al. .......... 342/22 |
| 5,170,170 | A |   | 12/1992 | Soumekh |
| 5,227,800 | A | * | 7/1993  | Huguenin et al. .......... 342/179 |
| 5,365,237 | A |   | 11/1994 | Johnson et al. |
| 5,438,336 | A | * | 8/1995  | Lee et al. .................... 342/174 |
| 5,557,108 | A | * | 9/1996  | Tumer .................... 250/390.04 |

(Continued)

OTHER PUBLICATIONS

David M. Sheen et al.; "Three-Dimensional Millimeter-Wave Imaging for Concealed Weapon Detection"; IEEE Transactions On Microwave Theory And Techniques, vol. 49, No. 9, Sep. 2001, pp. 1581-1592.

(Continued)

*Primary Examiner*—Bernarr E. Gregory (57) ABSTRACT

An inspection system uses microwave radiation to capture a microwave image of a transportable item. The system includes a transmit scanning panel including a transmit array of transmit antenna elements, each being programmable with a respective phase delay to direct a transmit beam of microwave radiation toward a target of the transportable item for transmission of the microwave radiation through the target. The system further includes a receive scanning panel including a receive array of receive antenna elements, each being programmable with a respective phase delay to receive a receive beam of microwave radiation from the target. A processor measures the amplitude and phase of the microwave radiation in the receive beam to determine a relative value of a pixel within the microwave image of the transportable item based on a reference value of the pixel.

20 Claims, 5 Drawing Sheets

U.S. PATENT DOCUMENTS

| | | | |
|---|---|---|---|
| 5,557,283 A * | 9/1996 | Sheen et al. ................. 342/179 |
| 5,940,030 A | 8/1999 | Hampel et al. |
| 5,940,045 A | 8/1999 | Belcher et al. |
| 5,982,326 A | 11/1999 | Chow et al. |
| 5,986,590 A | 11/1999 | Smith et al. |
| 6,037,908 A | 3/2000 | Phillips et al. |
| 6,043,786 A | 3/2000 | Vannatta et al. |
| 6,057,761 A | 5/2000 | Yukl |
| 6,130,641 A * | 10/2000 | Kraeutner et al. ........... 342/179 |
| 6,242,740 B1 * | 6/2001 | Luukanen et al. ........... 250/353 |
| 6,353,224 B1 * | 3/2002 | Sinclair et al. .............. 342/179 |
| 6,359,582 B1 * | 3/2002 | MacAleese et al. .......... 342/22 |
| 6,480,141 B1 * | 11/2002 | Toth et al. .................... 342/22 |
| 6,501,414 B2 | 12/2002 | Arndt et al. |
| 6,507,309 B2 * | 1/2003 | McMakin et al. ............ 342/22 |
| 6,549,166 B2 | 4/2003 | Bhattacharyya et al. |
| 6,642,889 B1 | 11/2003 | McGrath |
| 6,703,964 B2 * | 3/2004 | McMakin et al. ............ 342/22 |
| 6,876,322 B2 * | 4/2005 | Keller ......................... 342/22 |
| 6,894,636 B2 * | 5/2005 | Anderton et al. ............. 342/22 |
| 6,937,182 B2 * | 8/2005 | Lovberg et al. ............... 342/22 |
| 2003/0034916 A1 | 2/2003 | Kwon et al. |
| 2003/0189510 A1 * | 10/2003 | Anderton et al. ............. 342/22 |
| 2004/0056790 A1 | 3/2004 | Lovberg et al. |
| 2004/0080448 A1 | 4/2004 | Lovberg et al. |

OTHER PUBLICATIONS

P.F. Goldsmith, et al.; "Focal Plane Imaging Systems for Millimeter Wavelengths"; IEEE Transactions on Microwave Theory And Techniques, vol. 41, No. 10, Oct. 1993, pp. 1664-1675.

Tatsuo Nozokido, et al.; "Scanning Near-Field Millimeter-Wave Microscopy Using a Metal Slit as a Scanning Probe"; IEEE Transactions On Microwave Theory And Techniques, vol. 49, No. 3, Mar. 2001, pp. 491-499.

* cited by examiner

SYSTEM AND METHOD FOR INSPECTING TRANSPORTABLE ITEMS USING MICROWAVE IMAGING

CROSS-REFERENCE TO RELATED APPLICATIONS

This application is related by subject matter to U.S. application for patent Ser. No. 10/997,422, entitled "A Device for Reflecting Electromagnetic Radiation," U.S. application for patent Ser. No. 10/997,583, entitled "Broadband Binary Phased Antenna," both of which were filed on Nov. 24, 2004, and U.S. Pat. No. 6,965,340, entitled "System and Method for Security Inspection Using Microwave Imaging" which issued on Nov. 15, 2005.

This application is further related by subject matter to U.S. application for patent Ser. No. 11/088,536, entitled "System and Method for Efficient, High-Resolution Microwave Imaging Using Complementary Transmit and Receive Beam Patterns," U.S. application for patent Ser. No. 11/089,298, entitled "System and Method for Pattern Design in Microwave Programmable Arrays," U.S. application for patent Ser. No. 11/088,610, entitled "System and Method for Microwave Imaging Using an Interleaved Pattern in a Programmable Reflector Array," and U.S. application for patent Ser. No. 11/088,830, entitled "System and Method for Minimizing Background Noise in a Microwave Image Using a Programmable Reflector Array" all of which were filed on even date herewith.

BACKGROUND OF THE INVENTION

In response to an increasing threat of terrorism, inspection of persons and other transportable items for weapons and other types of contraband is becoming essential at security checkpoints, such as those found at airports, concerts, sporting events, courtrooms, federal buildings, schools and other types of public and private facilities potentially at risk from terrorist attacks. Conventional security inspection systems currently in place at security checkpoints include physical inspection, such as visual and/or tactile inspection, performed by security personnel, metal detectors and X-ray systems. However, physical inspection by security personnel is tedious, unreliable and invasive. In addition, metal detectors are prone to false alarms, and are not capable of detecting non-metallic objects, such as plastic or liquid explosives, plastic or ceramic handguns or knives and drugs. Furthermore, X-ray systems pose a health risk, particularly to those people who are repeatedly exposed to X-ray radiation, such as airport personnel, and X-ray systems are also not able detect certain materials/geometries, such as ceramic knives.

As a result of the need for improved security inspection systems, various microwave imaging systems have been proposed as an alternative to existing systems. Microwave radiation is generally defined as electromagnetic radiation having wavelengths between radio waves and infrared waves. An advantage of microwave radiation over X-ray radiation is that microwave radiation is non-ionizing, and therefore, poses no known health risks to people at moderate power levels. In addition, over the spectral band of microwave radiation, most dielectric materials, such as cardboard, plastic cloth, leather and dry wood are nearly transparent. Therefore, microwave imaging systems have the ability to penetrate wooden or plastic crates, luggage bags, envelopes, cloth bags and other types of transportable items.

At present, there are several microwave imaging techniques available. For example, one technique uses an array of microwave detectors to capture either passive microwave energy emitted by the target or reflected microwave energy reflected from the target in response to active microwave radiation of the target. A two-dimensional or three-dimensional image of a person or other item is constructed by scanning (moving) the array of detectors with respect to the item's position and/or adjusting the frequency (or wavelength) of the microwave energy being transmitted or detected. For example, an article by David M. Sheen et al., "Three-Dimensional Millimeter-Wave Imaging for Concealed Weapon Detection," IEEE Transactions on Microwave Theory and Techniques, Vol. 49, No. 9, September 2001, pp. 1581–1592 describes a three-dimensional holographic microwave imaging technique that uses a scanning bar to mechanically move a linear array of detectors to scan an item or person. The resulting measured data is used to reconstruct a holographic image of the item. However, such scanning systems typically require mechanically moving parts and/or intensive post-processing reconstruction of the image, both of which increase the cost and complexity of the microwave imaging system.

Another technique uses lenses to focus a beam of microwave radiation on the array of microwave detectors. This type of technique is described, for example, in the article P. F. Goldsmith, et al., "Focal Plane Imaging Systems for Millimeter Wavelengths," IEEE Transactions on Microwave Theory and Techniques, Vol. 41, No. 10, October 1993, pp. 1664–1675. However, microwave imaging systems that use lenses to focus the microwave energy typically have a limited field of view and small aperture size. In addition, the cost of the lens system may be prohibitively large in many applications.

Therefore, what is needed is a cost-effective and simple microwave imaging system for use in security inspection of transportable items that does not require any moving parts.

SUMMARY OF THE INVENTION

Embodiments of the present invention provide a set of scanning panels for use in a microwave imaging system to capture a microwave image of a transportable item. A transmit scanning panel includes a transmit array of transmit antenna elements, each being programmable with a respective phase delay to direct a transmit beam of microwave radiation toward a target of the transportable item for transmission therethrough. A receive scanning panel includes a receive array of receive antenna elements, each being programmable with a respective phase delay to receive a receive beam of microwave radiation from the target. A processor measures the amplitude and phase of the microwave radiation in the receive beam to determine a relative value of a pixel within an image of the transportable item based on a reference value of the pixel.

In one embodiment, at least one of the transmit and receive antenna elements are reflecting antenna elements. A microwave source transmits microwave radiation towards the transmit array of transmit antenna elements, which in turn reflects the microwave radiation based on the respective programmed phase delays to direct the transmit beam of microwave radiation toward the target. The receive array of receive antenna elements is configured to receive the receive beam from the target and reflect the receive beam towards a microwave receiver based on an additional respective phase delay associated with the receive antenna elements in the receive array.

In a further embodiment, an imaging region is defined between the transmit scanning panel and the receive scanning panel. The processor determines the relative value of the pixel using scattering properties of the target when the target is spatially located near an edge of the imaging region. When the target is spatially located near a center of the imaging region, the processor determines the relative value of the pixel using transmissive properties of the target.

In still a further embodiment, a memory stores the reference value of the pixel measured at a spatial location associated with the target without the presence of the transportable item. The processor determines a current value of the pixel based on the amplitude and phase of the microwave radiation in the receive beam. The relative value of the pixel is determined by computing an absolute value of the complex difference between the current value and the reference value.

BRIEF DESCRIPTION OF THE DRAWINGS

The disclosed invention will be described with reference to the accompanying drawings, which show important sample embodiments of the invention and which are incorporated in the specification hereof by reference, wherein.

DETAILED DESCRIPTION OF THE EXEMPLARY EMBODIMENTS

As used herein, the terms microwave radiation and microwave illumination each refer to the band of electromagnetic radiation having wavelengths between 0.3 mm and 30 cm, corresponding to frequencies of about 1 GHz to about 1,000 GHz. Thus, the terms microwave radiation and microwave illumination each include traditional microwave radiation, as well as what is commonly known as millimeter-wave radiation.

Figure 1:
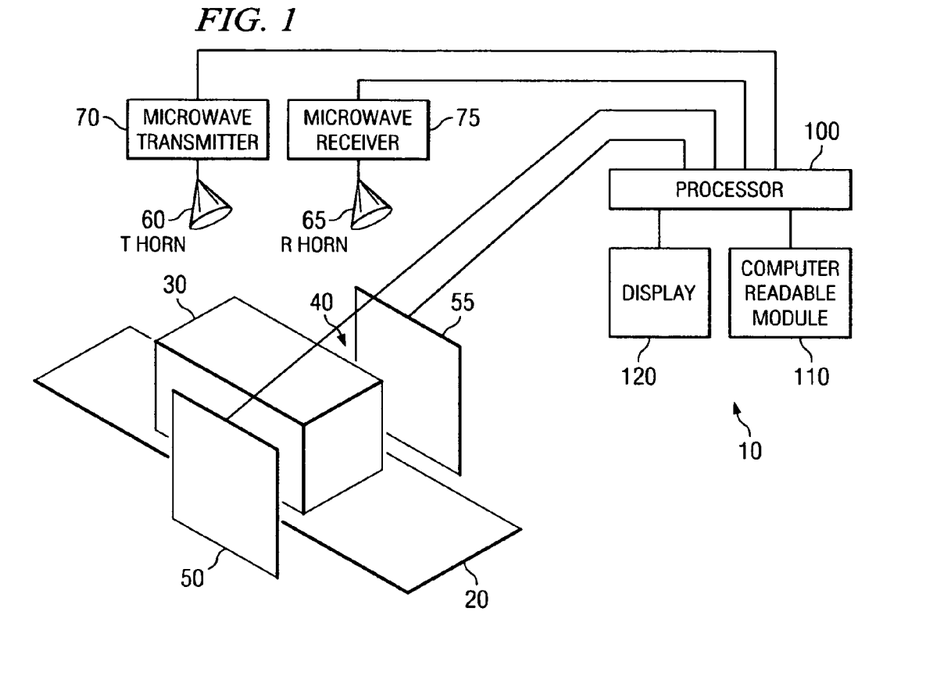
FIG. 1 is a schematic diagram of a simplified exemplary microwave security inspection system for imaging transportable items, in accordance with embodiments of the present invention.

FIG. 1 is a schematic diagram of a simplified exemplary microwave security inspection system 10, in accordance with embodiments of the present invention. The microwave security inspection system 10 includes a conveyor belt 20 on which a transportable item 30 is placed. The microwave security inspection system 10 further includes a set of scanning panels 50 and 55. A first scanning panel (e.g., scanning panel 50) is a transmit scanning panel that is capable of transmitting microwave radiation towards the transportable item 30. A second scanning panel (e.g., scanning panel 55) is a receive scanning panel that is capable of receiving microwave radiation scattered from or transmitted through the transportable item 30. An imaging region 40 is defined between the transmit scanning panel 50 and the receive scanning panel 55 through which the microwave radiation passes from the transmit scanning panel 55 to the receive scanning panel 55. The conveyor belt 20 controls movement of the transportable item 30 through the imaging region 40.

In one embodiment, one or more of the scanning panels 50 and 55 includes an active transmitter/receiver array composed of active antenna elements. The transmit scanning panel 50 includes active antenna elements capable of producing and transmitting microwave radiation towards a target position in the imaging region 40 associated with the transportable item 30, while the receive scanning panel 55 includes active antenna elements capable of receiving and capturing microwave radiation scattered at or transmitted through the target position. For example, each of the active antenna elements in the active transmit array (scanning panel 50) is individually programmable with a respective phase shift to steer a beam of microwave radiation towards the target position. In addition, each of the active antenna elements in the active receive array (scanning panel 55) is individually programmable with a respective phase shift to receive the scattered/transmitted microwave radiation from the target position.

In another embodiment, as illustrated in FIG. 1, one or more of the scanning panels 50 and 55 includes a passive programmable reflector array composed of reflecting antenna elements. A transmit microwave antenna (horn) 60 transmits a transmit beam of microwave radiation towards the transmit scanning panel 50. Each of the reflecting antenna elements in the transmit scanning panel 50 is programmed with a respective binary or continuous phase delay to direct the transmit beam of microwave radiation towards a target position in the imaging region 40 associated with the transportable item 30. Microwave radiation scattered from or transmitted through the transportable item 30 at the target position is received by the receive scanning panel 55. Each of the reflecting antenna elements in the receive scanning panel 55 is programmed with a respective binary or continuous phase delay to direct microwave radiation received from the transportable item 30 towards a receive microwave antenna (horn) 65.

It should be understood that in other embodiments, the transmit and receive scanning panels 50 and 55, respectively, may be transmission arrays, in which the horns 60 and 65 are located behind the respective scanning panels 50 and 55 to illuminate the transmit and receive scanning panels 50 and 55, respectively, from behind (i.e., the arrays 50 and 55 are situated between the item 30 and the horns 60 and 65). Furthermore, it should be understood that in other embodiments, hybrid designs are possible where one of the arrays 50 or 55 is a reflector array illuminated in front and the other array 50 or 55 is a transmission array illuminated from behind.

Antenna element 60 is controlled by a microwave transmitter 70, while antenna element 65 is controlled by a microwave receiver 75. In one embodiment, microwave transmitter 70 drives the antenna element 60 to illuminate the transmit scanning panel 50, which transmits the transmit beams of microwave radiation towards target positions in the imaging region 40 associated with the transportable item 30 (e.g., within or on the item). In another embodiment, microwave receiver 75 monitors the received microwave radiation reflected from the receive scanning panel 55, measures the magnitude and/or the phase of the reflected microwave radiation as a function of the direction of the received microwave radiation and records microwave measurements corresponding to a characteristic of the response of the transportable item 30 to the microwave radiation. In one embodiment, the microwave measurements include amplitude and phase measurements of the wavefront scattered from the transportable item 30.

The measurements recorded by the microwave receiver 75 or the receive scanning panel 55 (if the scanning panels include active antenna elements) are transmitted to a processor 100 which operates to construct a microwave image of the transportable item 30 based on the measurements. In general, the processor 100 receives a complex value (amplitude and phase) for each target position in the imaging region, and combines the complex values to produce the microwave image of the transportable item 30. For example, the processor 100 associates a received complex value with a target position associated with the transportable item 30 and populates the value of a pixel in the microwave image with the received complex value. The position of the populated pixel in the microwave image corresponds to the target position associated with the transportable item 30. In operation, the microwave security inspection system 10 can operate at frequencies that enable millions of targets in the imaging region to be scanned per second. Thus, the speed at which the conveyor belt 20 operates is slow enough to allow a complete microwave image to be taken as the transportable item 30 moves through the imaging region 40.

In embodiments in which the scanning panels 50 and 55 are passive reflector arrays, the receive microwave antenna 65 is capable of combining the received microwave radiation reflected from each antenna element in the receive scanning panel 55 to produce a value of the effective amplitude and phase of the microwave radiation at the target position. The complex value is passed to the processor 100, which uses the complex value to determine the value of a pixel corresponding to the target position.

In addition, the processor 100 operates to program the phase delays or phase shifts of each of the individual antenna elements in the scanning panels 50 and 55 to illuminate multiple targets in the imaging region 40 associated with the transportable item 30 with microwave radiation and/or receive reflected microwave radiation from multiple targets associated with the transportable item 30. Thus, the processor 100 in conjunction with the scanning panels 50 and 55 operates to scan the transportable item 30.

The processor 100 includes any hardware, software, firmware, or combination thereof for controlling the scanning panels 50 and 55 and microwave antennas 60 and 65 and processing the received microwave radiation from the transportable item 30 to construct a microwave image of the transportable item 30. For example, the processor 100 may include one or more microprocessors, microcontrollers, programmable logic devices, digital signal processors or other type of processing devices that are configured to execute instructions of a computer program, and one or more memories (e.g., cache memory) that store the instructions and other data used by the processor 100. However, it should be understood that other embodiments of the processor 100 may be used. In addition, the processor 100 can include multiple processors or be a single general-purpose processor capable of executing a number of algorithms.

The measurements are used by the processor 100 to produce microwave image data (e.g., pixel or voxel values) representing the microwave image of the transportable item 30. The microwave image data can be stored in a computer-readable medium 110. The computer-readable medium 110 can be a memory device, such as random access memory (RAM), read-only memory (ROM), flash memory, EEPROM, disk drive, compact disk, floppy disk or tape drive, or any other type of storage device. Additional processing information can also be stored on the computer-readable medium 110 and accessed by the processor 100. For example, such processing information can include various processing parameters, such as algorithms that can be used to process the measurements and produce the microwave image data.

The resulting microwave image of the transportable item 30 can be output from the memory 110 by the processor 100 to a display 120 to display the microwave image of the transportable item 30. In one embodiment, the display 120 is a two-dimensional display for displaying a three-dimensional microwave image of the transportable item 30 or one or more two-dimensional microwave images of the transportable item 30. In another embodiment, the display 120 is a three-dimensional display capable of displaying a three-dimensional microwave image of the transportable item 30.

Figure 2:
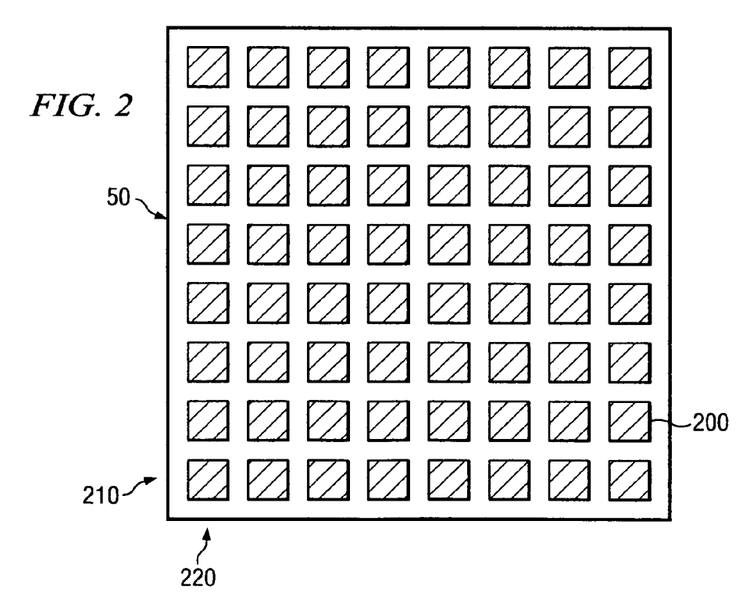
FIG. 2 is a schematic diagram of a simplified exemplary scanning panel for use in the inspection system of FIG. 1, in accordance with embodiments of the present invention.

FIG. 2 is a schematic diagram of a simplified exemplary scanning panel 50 for use in the inspection system of FIG. 1, in accordance with embodiments of the present invention. The scanning panel 50 in FIG. 2 is a reflector antenna array that includes distinct reflecting antenna elements 200 that reflect electromagnetic radiation with varying phase depending on their impedance state, as described in U.S. patent application Ser. No. 10/997,422. Ideally, the reflecting antenna elements 200 reflect electromagnetic radiation with a phase shift of 180 degrees (binary phase-shifted) when their impedance is high relative to when their impedance is low. The reflecting antenna elements 200 are individually controllable and the reflector antenna array is typically supported by driver electronics (not shown in FIG. 2). The reflector antenna array is formed on and/or in a substrate, such as a printed circuit board. In one example, the reflector antenna array has a surface area of approximately one meter square and is covered with 10,000 to 100,000 individually controllable reflecting antenna elements 200 arranged in rows 210 and columns 220.

Each reflecting antenna element 200 includes an antenna and a non-ideal switching device. The antenna functions to absorb or reflect a beam of electromagnetic radiation to varying degrees depending on the impedance level of the reflecting antenna element 200. Example antenna types that can be incorporated into a reflector antenna array include patch, dipole, monopole, loop, and dielectric resonator type antennas. In reflector antenna array applications, the antennas are often formed in a single plane on the surface of the reflector antenna array substrate. The antennas have an impedance characteristic that is a function of the antenna design parameters. Design parameters of antennas include but are not limited to, physical attributes such as the dielectric material of construction, the thickness of the dielectric material, shape of the antenna, length and width of the antenna, feed location, and thickness of the antenna metal layer.

The non-ideal switching device changes the impedance state of the reflecting antenna element 200 by changing its resistive state. A low resistive state (e.g., a closed or "short"

circuit) translates to a low impedance. Conversely, a high resistive state (e.g., an open circuit) translates to a high impedance. A switching device with ideal performance characteristics (referred to herein as an "ideal" switching device) produces effectively zero impedance (Z=0) when its resistance is at its lowest state and effectively infinite impedance (Z=∞) when its resistance is at its highest state. As described herein, a switching device is "on" when its impedance is at its lowest state (e.g., $Z_{on}$=0) and "off" when its impedance is at its highest state (e.g., $Z_{off}$=∞). Because the on and off impedance states of an ideal switching device are effectively $Z_{on}$=0 and $Z_{off}$=∞, an ideal switching device is able to provide the maximum phase shift without absorption of electromagnetic radiation between the on and off states. That is, the ideal switching device is able to provide switching between 0 and 180 degree phase states. In the case of an ideal switching device, maximum phase-amplitude performance can be achieved with an antenna that exhibits any finite non-zero impedance.

In contrast to an ideal switching device, a "non-ideal" switching device is a switching device that does not exhibit on and off impedance states of $Z_{on}$=0 and $Z_{off}$=∞, respectively. Rather, the on and off impedance states of a non-ideal switching device are typically, for example, somewhere between $0<|Z_{on}|<|Z_{off}|<\infty$. However, in some applications, the on and off impedance states may even be $|Z_{off}|<=|Z_{on}|$. A non-ideal switching device may exhibit ideal impedance characteristics within certain frequency ranges (e.g., <10 GHz) and highly non-ideal impedance characteristics at other frequency ranges (e.g., >20 GHz).

Because the on and off impedance states of a non-ideal switching device are somewhere between $Z_{on}$=0 and $Z_{off}$=∞, the non-ideal switching device does not necessarily provide the maximum phase state performance regardless of the impedance of the corresponding antenna, where maximum phase state performance involves switching between 0 and 180 degree phase states. In accordance with the invention, the antennas of a reflector antenna array that utilizes non-ideal switching devices are specifically designed to provide optimal phase performance, where the optimal phase state performance of a reflecting antenna element is the point at which the reflecting element is closest to switching between 0 and 180 degree phase-amplitude states. In an embodiment, to achieve optimal phase state performance, the antennas are configured as a function of the impedance of the non-ideal switching devices. For example, the antennas are designed such that the impedance of the antennas is a function of impedance characteristics of the non-ideal switching devices.

Further, the antennas are configured as a function of the impedance of the non-ideal switching devices in the on state, $Z_{on}$, and the impedance of the non-ideal switching device in the off state, $Z_{off}$. In a particular embodiment, the phase state performance of a reflecting element is optimized when the antennas are configured such that the impedance of each antenna is conjugate to the square root of the impedance of the non-ideal switching devices when in the on and off impedance states, $Z_{on}$ and $Z_{off}$. Specifically, the impedance of each antenna is the complex conjugate of the geometric mean of the on and off impedance states, $Z_{on}$ and $Z_{off}$, of the corresponding non-ideal switching device. This relationship is represented as:

$$Z_{antenna}^* = \sqrt{Z_{on} Z_{off}} \quad (1)$$

The above-described relationship is derived using the well-known formula for the complex reflection coefficient between a source impedance and a load impedance. Choosing the source to be the antenna and the load to be the non-ideal switching device, the on-state reflection coefficient is set to be equal to the opposite of the off-state reflection coefficient to arrive at equation (1).

Designing an antenna that exhibits optimal phase-amplitude performance involves determining the on and off impedances, $Z_{on}$ and $Z_{off}$ of the particular non-ideal switching device that is used in the reflecting antenna elements 200. Design parameters of the antenna are then manipulated to produce an antenna with an impedance that matches the relationship expressed in equation (1) above. An antenna that satisfies equation (1) can be designed as long as $Z_{on}$ and $Z_{off}$ are determined to be distinct values.

Types of switching devices that exhibit non-ideal impedance characteristics over the frequency band of interest include low cost surface mount devices such as surface mount field effect transistors (FETs) and surface mount diodes. Although surface mount FETs exhibit non-ideal impedance characteristics over the frequency band of interest, they are relatively inexpensive and can be individually packaged for use in reflector antenna array applications.

Figure 3:
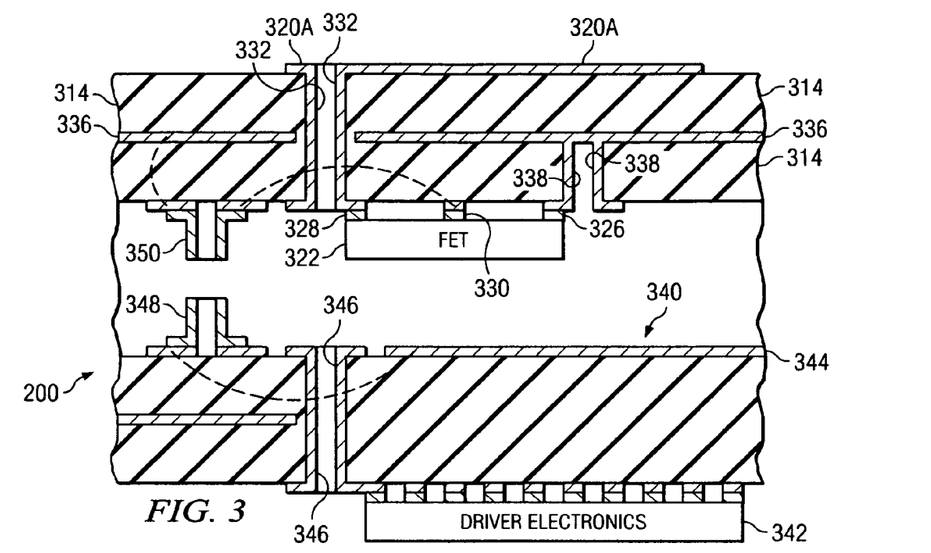
FIG. 3 is a cross-sectional view of an exemplary antenna element of the scanning panel of FIG. 2, in accordance with embodiments of the present invention.

In an embodiment, the antenna elements 200 in the reflector antenna array 50 include planar patch antennas. FIG. 3 is a cross-sectional view of an antenna element 200 that utilizes a planar patch antenna 320a with a surface mounted FET 322 as the non-ideal switching device, in accordance with embodiments of the present invention. The reflecting antenna element 200 is formed on and in a printed circuit board substrate 314 and includes the surface mounted FET 322, a patch antenna 320a, a drain via 332, a ground plane 336 and a source via 338. The surface mounted FET 322 is mounted on the opposite side of the printed circuit board substrate 314 as the planar patch antenna 320a and the ground plane 336 is located between the planar patch antenna 320a and the surface mounted FET 322. The drain via 332 connects the drain 328 of the surface mounted FET 322 to the planar patch antenna 320a and the source via 338 connects the source 326 of the surface mounted FET 322 to the ground plane 336.

In a working product, the reflector antenna array is connectable to a controller board 340 that includes driver electronics. An example controller board 340 is also depicted in FIG. 3 and includes a ground plane 344, a drive signal via 346, and driver electronics 342. The controller board 340 also includes connectors 348 that are compatible with connectors 350 of the reflector antenna array. The connectors 348 of the two boards can be connected to each other, for example, using wave soldering. It should be understood that in other embodiments, the FET 322 can be surface mounted on the same side of the printed circuit board substrate 314 as the planar patch antenna 320a. Additionally, the driver electronics 342 can be soldered directly to the same printed circuit board in which the reflecting antenna element 200 is built.

In a reflector antenna array that utilizes FETs as the non-ideal switching devices, the beam-scanning speed that can be achieved depends on a number of factors including signal-to-noise ratio, crosstalk, and switching time. In the case of a FET, the switching time depends on gate capacitance, drain-source capacitance, and channel resistance (i.e., drain-source resistance). The channel resistance is actually space-dependent as well as time-dependent. In order to minimize the switching time between impedance states, the drain of the FET is preferably DC-shorted at all times. The drain is preferably DC-shorted at all times because floating the drain presents a large off-state channel resistance as well as a large drain-source capacitance due to the huge parallel-plate area of the patch antenna. This implies that the antenna is preferably DC-shorted but one wishes the only "rf short" the antenna sees be at the source. Therefore, the additional antenna/drain short must be optimally located so as to minimally perturb the antenna.

In other embodiments, the reflector antenna array can include continuous phase-shifted antenna elements 200 by replacing the FETs with variable capacitors (e.g., Barium Strontium Titanate (BST) capacitors). With the variable capacitor loaded patches, continuous phase shifting can be achieved for each antenna element 200, instead of the binary phase shifting produced by the FET loaded patches. Continuous phased arrays can be adjusted to provide any desired phase shift in order to steer a microwave beam towards any direction in a beam scanning pattern.

Figure 4:
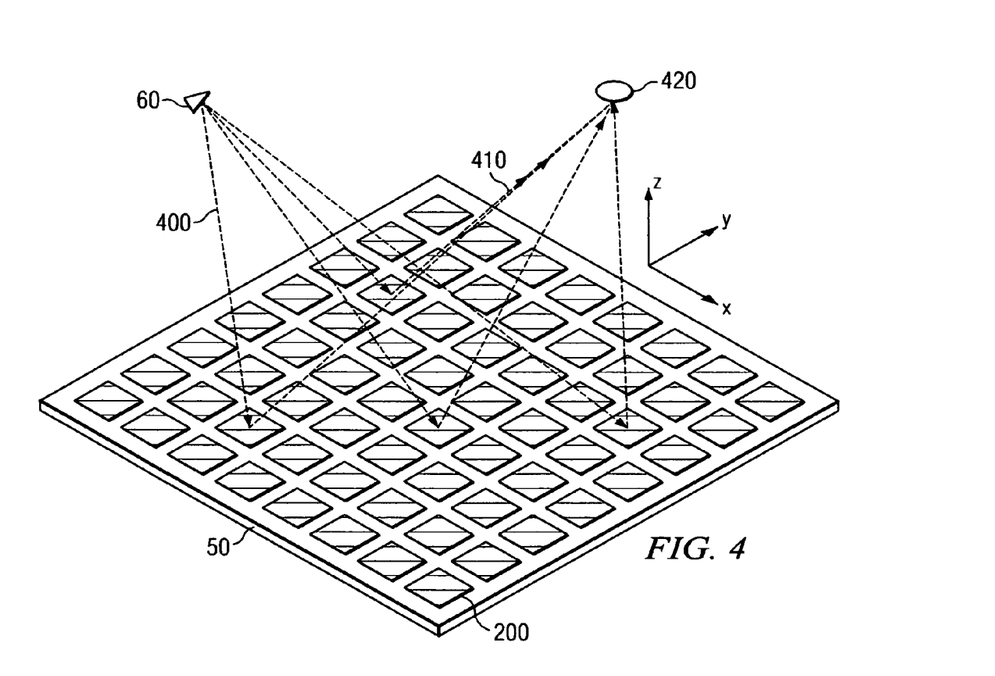
FIG. 4 is a schematic diagram of a top view of an exemplary scanning panel for reflecting microwave radiation, in accordance with embodiments of the present invention.

FIG. 4 is a schematic diagram of a top view of an exemplary scanning panel 50 for reflecting microwave radiation, in accordance with embodiments of the present invention. In FIG. 4, microwave radiation 400 transmitted from a microwave antenna 60 is received by various antenna elements 200 in the scanning panel 50. The antenna elements 200 are each programmed with a respective phase delay to direct reflected microwave radiation 410 towards a target 420. The phase delays are selected to create positive interference of the reflected microwave radiation 410 from each of the antenna elements 200 at the target 420. Ideally, the phase shift of each of the antenna elements 200 is adjusted to provide the same phase delay for each path of the reflected microwave radiation 410 from the source (antenna element 200) to the target 420.

Figure 5:
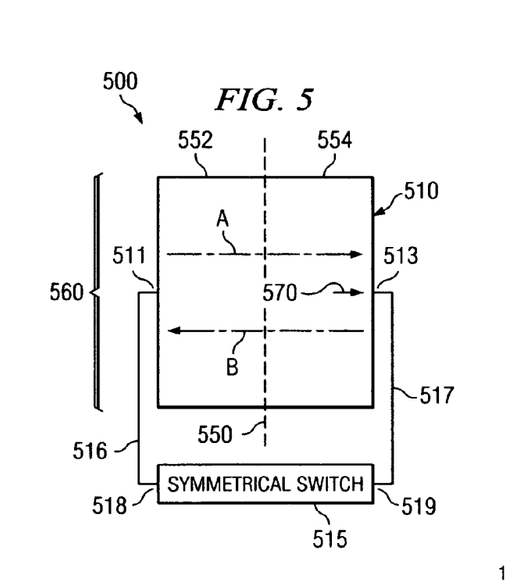
FIG. 5 illustrates an exemplary active antenna element for use in a scanning panel of the inspection system shown in FIG. 1.

In further embodiments, the scanning panel is an active transmit/receive array including active antenna elements. An example of an active antenna element 500 for use in an transmit/receive array is shown in FIG. 5 and described in co-pending and commonly assigned U.S. patent application Ser. No. 10/997,583. The active antenna element 500 is a broadband binary phased antenna element including an antenna 510 connected to a respective switch 515. The switch 515 can be, for example, a single-pole double-throw (SPDT) switch or a double-pole double-throw (DPDT) switch. The operating state of the switch 515 controls the phase of the respective antenna element 500. For example, in a first operating state of the switch 515, the antenna element 500 may be in a first binary state (e.g., 0 degrees), while in a second operating state of the switch 515, the antenna element 500 may be in a second binary state (e.g., 180 degrees). The operating state of the switch 515 defines the terminal connections of the switch 515. For example, in the first operating state, terminal 518 may be in a closed (short circuit) position to connect feed line 516 between the antenna 510 and the switch 515, while terminal 519 may be in an open position. The operating state of each switch 515 is independently controlled by a control circuit (not shown) to individually set the phase of each antenna element 500.

As used herein, the term symmetric antenna 510 refers to an antenna that can be tapped or fed at either of two feed points 511 or 513 to create one of two opposite symmetric field distributions or electric currents. As shown in FIG. 12, the two opposite symmetric field distributions are created by using a symmetric antenna 510 that is symmetric in shape about a mirror axis 550 thereof. The mirror axis 550 passes through the antenna 510 to create two symmetrical sides 552 and 554. The feed points 511 and 513 are located on either side 552 and 554 of the mirror axis 550 of the antenna 510. In one embodiment, the feed points 511 and 513 are positioned on the antenna 510 substantially symmetrical about the mirror axis 550. For example, the mirror axis 550 can run parallel to one dimension 560 (e.g., length, width, height, etc.) of the antenna 510, and the feed points 511 and 513 can be positioned near a midpoint 570 of the dimension 560. In FIG. 12, the feed points 511 and 513 are shown positioned near a midpoint 570 of the antenna 510 on each side 552 and 554 of the mirror axis 550.

The symmetric antenna 510 is capable of producing two opposite symmetric field distributions, labeled A and B. The magnitude (e.g., power) of field distribution A is substantially identical to the magnitude of field distribution B, but the phase of field distribution A differs from the phase of field distribution B by 180 degrees. Thus, field distribution A resembles field distribution B at ±180° in the electrical cycle.

The symmetric antenna 510 is connected to the symmetric switch 515 via feed lines 516 and 517. Feed point 511 is connected to terminal 518 of the symmetric switch 515 via feed line 516, and feed point 513 is connected to terminal 519 of the symmetric switch 515 via feed line 517. As used herein, the term symmetric switch refers to either a SPDT or DPDT switch in which the two operating states of the switch are symmetric about the terminals 518 and 519.

For example, if in a first operating state of a SPDT switch, the impedance of channel $\alpha$ is 10$\Omega$ and the impedance of channel $\beta$ is 1 k$\Omega$, then in the second operating state of the SPDT switch, the impedance of channel $\alpha$ is 1 k$\Omega$ and the impedance of channel $\beta$ is 10$\Omega$. It should be understood that the channel impedances are not required to be perfect opens or shorts or even real. In addition, there may be crosstalk between the channels, as long as the crosstalk is state-symmetric. In general, a switch is symmetric if the S-parameter matrix of the switch is identical in the two operating states of the switch (e.g., between the two terminals 518 and 519).

It should be understood that other types of antenna elements may be used to transmit, receive and/or reflect microwave radiation to and from a transportable item being scanned. In addition, it should be understood that the size and shape of the scanning panels is dependent upon the particular application of the microwave security inspection system. Furthermore, in other embodiments, multiple transmit and/or receive scanning panels may be used to scan the transportable item.

Figure 6A:
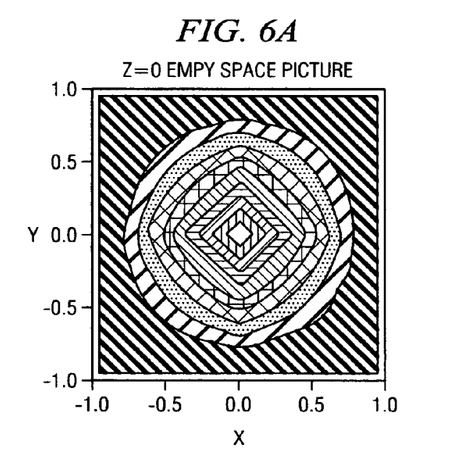
FIGS. 6A and 6B are sectional images illustrating an exemplary scan of the imaging region between the arrays without a transportable item present, in accordance with embodiments of the present invention.
Figure 6B:
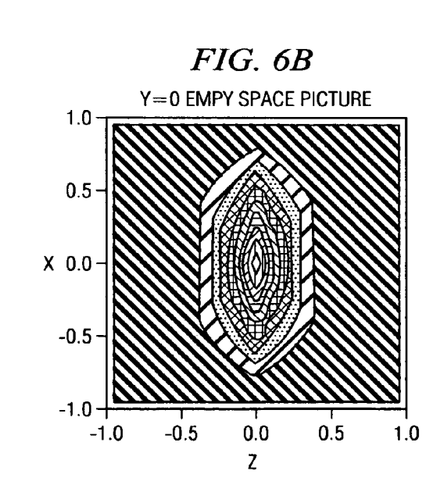

Referring now to FIGS. 6A and 6B, which will be discussed in connection with the microwave security inspection system shown in FIG. 1, a scan of the imaging region 40 between the transmit and receive scanning panels 50 and 55 without any transportable item 30 present in the imaging region 40 produces an image with a mixture of transmitted and scattered microwave radiation. Targets near the center of the imaging region 40 are imaged primarily by transmission of microwave radiation through the targets (based on the transmissive properties of the target), while targets near the periphery of the imaging region 40 are imaged primarily by scattered microwave radiation (based on the scattering properties of the target). Thus, without algorithmic processing, an opaque object near the center of the imaging region 40 appears dark against a bright background. Similarly, without algorithmic processing, a shiny object in the microwave portion of the electromagnetic (EM) spectrum that is located near the periphery of the imaging region 40 appears bright against a dark background.

FIGS. 6A and 6B are sectional images illustrating an exemplary scan of the imaging region 40 between the arrays 50 and 55 without any transportable items 30 present, in accordance with embodiments of the present invention. In FIGS. 6A and 6B, the x-axis corresponds to the direction of conveyor belt 20 motion, the z-axis corresponds to the direction from the transmit scanning panel 50 to the receive scanning panel 55 and the y-axis corresponds to the vertical direction orthogonal to the plane of the conveyor belt 20. If both scanning panels 50 and 55 are squares of side two meters and arranged parallel to each other in the y-direction and two meters apart in the z-direction, an origin (0,0,0) can be defined as the point midway between the centers of each scanning panel 50 and 55. A scan of the imaging region 40 between the two scanning panels 50 and 55 without any transportable items 30 present produces a volume image that is bright near the origin and dark toward the periphery. Two cross-sectional planes of this volume image are shown in FIGS. 6A and 6B.

It should be noted that the sectional images illustrated in FIGS. 6A and 6B represent only the amplitude of the microwave signal. However, in other embodiments, both the amplitude and phase or equivalently real (in-phase) and imaginary (quadrature) components of the microwave signal are recorded.

With both transmitted and scattered microwave radiation present in the volume image, the image lacks a consistent contrast (bright background or dark background) throughout. In order to render a microwave image with a consistent sense of contrast to the viewer, the image is processed prior to display to compensate for the different types of radiation (transmitted and scattered).

Figure 7:
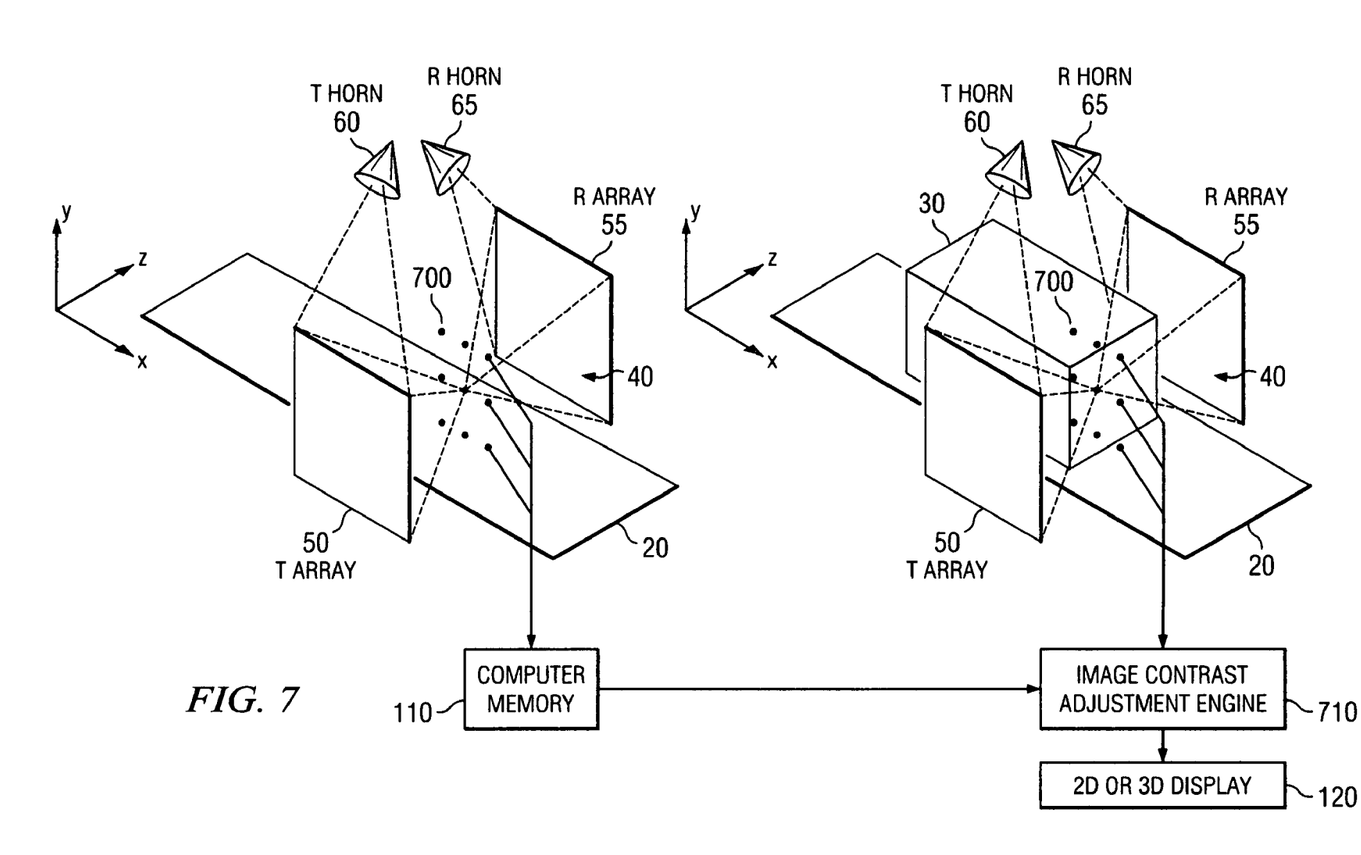
FIG. 7 is a schematic diagram illustrating an exemplary operation of the microwave security inspection system, in accordance with embodiments of the present invention.

FIG. 7 is a schematic diagram illustrating an exemplary operation of the microwave security inspection system 10 to produce a microwave image with a consistent contrast, in accordance with embodiments of the present invention. At an initial time, a calibration procedure is performed in which the transmit microwave antenna (horn) 60 illuminates the transmit scanning panel 50 with coherent (monochromatic) microwave radiation to scan the imaging region 40 at target 700 positions in the imaging region 40 with no transportable item present on the conveyor belt 20. Microwave radiation scattered or transmitted through the imaging region 40 from the targets 700 is received by the receive scanning panel 55 and directed towards the receive microwave antenna (horn) 65.

Each pixel (2D scan) or voxel (3D scan) is addressed by both the transmit and receive scanning panels 50 and 55 by loading the appropriate binary phases to each of the antenna elements in the scanning panels 50 and 55. The resulting scan produces a reference ("background") image of the imaging region 40, which is stored in the memory 110. Thus, for each pixel or voxel in the reference image, a complex value (magnitude and phase) representing the transmitted and/or scattered microwave radiation is stored in the memory 110. This calibration procedure is performed infrequently (e.g., at system initialization).

At a later time, a scan of the imaging region 40 at the same target 700 positions is performed with a transportable item 30 present on the conveyor belt 20. This latter scan produces a current image of the imaging region 40. The current image and the reference image are input to an image contrast adjustment engine 710 within the processor 100 to subtract the current image pixel (or voxel) values from the corresponding reference image pixel (or voxel) values, and display on the display 120 the magnitudes (absolute values or squares thereof) of the complex differences as an output microwave image that is consistent in contrast. For example, in one embodiment, for each pixel (or voxel), the image contrast adjustment engine 710 determines the relative value of the pixel (or voxel) by computing an absolute value of the complex difference between the current value and the reference value.

The scan of the transportable item 30 can be performed while the transportable item 30 is stationary and located within the imaging region 40 or while the transportable item 30 is in motion (e.g., constant velocity provided by the conveyor belt 20). The position of the transportable item 30 in the x-y-z space can be represented by the equation:

$$x_{item} = x_{system} - vt, \quad (1)$$

where $x_{item}$ is the x-coordinate within he fixed item, i.e., within the transportable item 30 when the transportable item 30 is stationary, $x_{system}$ is a fixed x-coordinate of the inspection system, v is the conveyor belt 20 velocity and t is the amount of time elapsed from the commencement of the scan. If an operator of the microwave security inspection system stops the transportable item (v=0) and performs a stationary volume scan, $x_{item} = x_{system}$.

However, if the transportable item is in motion during the scan, in one embodiment, the system 10 can volume-scan a single yz-plane ($x_{system}=0$ or any constant), and the conveyor belt 20 can provide the x-scan. In another embodiment, the system 10 can volume-scan in $x_{system}$-y-z space and the processor 100 can convert the volume-scan into $x_{item}$-y-z space using Equation (1). In operation, the system 10 is capable of scanning a million voxels per second, so the elapsed time from start to finish of a typical transportable item is less than a second. Since typical conveyor velocities are 10–40 cm/s, the processor correction can easily be applied with high accuracy (e.g., better than the ~half-wavelength resolution of the microwave system). Therefore, item motion does not degrade image quality.

Figure 8:
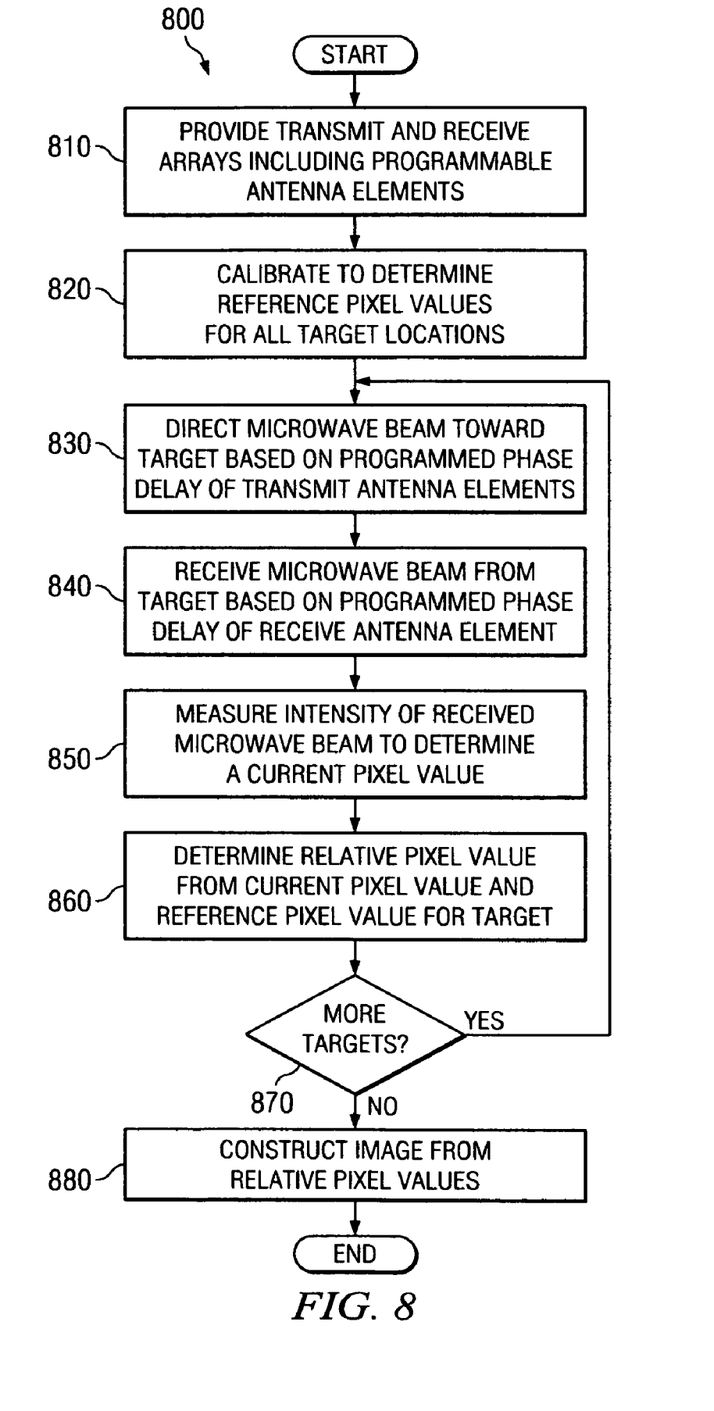
FIG. 8 is a flow chart illustrating an exemplary process for rendering a microwave image of a transportable item, in accordance with embodiments of the present invention.

FIG. 8 is a flow chart illustrating an exemplary process 800 for rendering a microwave image of a transportable item, in accordance with embodiments of the present invention. Initially, a set of scanning panels, including a transmit array and a receive array, each including programmable antenna elements, is provided for use in a microwave security inspection system at block 810. At block 820, a calibration process is performed to determine reference pixel values for target positions in the microwave security inspection system. For example, for each target in an imaging region defined between the transmit array and receive array, each of the antenna elements in the transmit array is programmed with a respective phase delay to direct a transmit beam of microwave radiation towards the target. Transmitted and/or scattered microwave radiation from the target is received at the receive array in a receive beam by programming each of the antenna elements in the receive array with a respective phase delay. The amplitude and phase of the microwave radiation in the receive beam is used to determine a reference pixel (or voxel) value within an image of the imaging region, in which the reference pixel spatially corresponds to the target position in the imaging region.

Once the calibration process is complete, a microwave image of a transportable item placed in the microwave security inspection system is rendered by programming each of the antenna elements in the transmit array with a respective phase delay to direct a transmit beam of microwave radiation towards one of the same targets (i.e., a particular position in the x-y-z imaging region space) for which a reference pixel value was obtained during the calibration process at step 830. At step 840, transmitted and/or scattered microwave radiation from the target is received at the receive array in a receive beam by programming each of the antenna elements in the receive array with a respective phase delay. At step 850, the amplitude and phase of the microwave radiation in the receive beam is used to determine a current pixel (or voxel) value within the image of the transportable item, in which the current pixel spatially corresponds to the target position in the imaging region.

A relative pixel value for the target is determined at step 860 from the current pixel value and reference pixel value. For example, the relative pixel (or voxel) value can be determined by computing an absolute value of the complex difference between the current pixel value and the reference pixel value for the target. At step 870, this process is repeated for each target for which a reference pixel value was obtained during the calibration process. At step 880, the microwave image of the transportable item is constructed from the relative pixel values computed for all of the targets.

As will be recognized by those skilled in the art, the innovative concepts described in the present application can be modified and varied over a wide rage of applications. Accordingly, the scope of patents subject matter should not be limited to any of the specific exemplary teachings discussed, but is instead defined by the following claims.

We claim:

1. A microwave inspection system for inspecting transportable items, comprising:
    a transmit scanning panel including a transmit array of transmit antenna elements, each of the transmit antenna elements being programmably controllable to implement a respective phase delay to direct a transmit beam of microwave radiation toward a target of the transportable item for transmission therethrough;
    a receive scanning panel including a receive array of receive antenna elements, each of the receive antenna elements being programmably controllable to implement a respective phase delay to receive a receive beam of microwave radiation from the target; and
    a processor operable to measure an amplitude and phase of the microwave radiation in the receive beam to determine a relative value of a pixel within an image of the transportable item based on a reference value of the pixel.

2. The system of claim 1, wherein each of the transmit array and the receive array is a reflector antenna array, and wherein the transmit antenna elements and the receive antenna elements are reflecting antenna elements.

3. The system of claim 2, wherein the transmit antenna elements are configured to receive microwave radiation from a microwave source and reflect the microwave radiation based on the respective programmed phase delays to direct the transmit beam of microwave radiation toward the target.

4. The system of claim 3, wherein the receive antenna elements are further configured to receive the receive beam from the target and reflect the receive beam towards a receive microwave antenna.

5. The system of claim 1, wherein at least one of the transmit array and the receive array is an active array.

6. The system of claim 1, wherein the transmit scanning panel is capable of simultaneously directing multiple microwave beams of different frequencies towards different targets of the transportable item.

7. The system of claim 1, further comprising:
    an imaging region defined between the transmit scanning panel and the receive scanning panel.

8. The system of claim 7, further comprising:
    a conveyor belt for moving the transportable item through the imaging region.

9. The system of claim 8, wherein the processor is operable to determine the relative value of the pixel using transmissive properties of the target when the target is spatially located near a center of the imaging region.

10. The system of claim 7, wherein the processor is operable to determine the relative value of the pixel using scattering properties of the target when the target is spatially located near an edge of the imaging region.

11. The system of claim 7, wherein the reference value of the pixel is measured at a spatial location in the imaging region associated with the target without the presence of the transportable item, and wherein the system further comprises:
    a memory for storing the reference value of the pixel.

12. The system of claim 11, wherein the processor is operable to determine a current value of the pixel based on the amplitude and phase of the microwave radiation in the receive beam, and wherein the processor is further operable to determine the relative value of the pixel by computing an absolute value of the complex difference between the current value and the reference value.

13. The system of claim 1, wherein the pixel is a voxel.

14. A method for inspection of transportable items, comprising:
    providing a transmit array including a plurality of transmit antenna elements and a receive array including a plurality of receive antenna elements, each of the transmit antenna elements and the receive antenna elements being programmably controllable to implement a respective phase delay;
    directing a transmit beam of microwave radiation towards a target of a transportable item for transmission therethrough based on the phase delay of each of the transmit antenna elements;
    receiving a receive beam of microwave radiation from the target at the receive array based on the phase delay of each of the receive antenna elements;
    measuring an amplitude and phase of the microwave radiation in the receive beam to determine a current value of the pixel; and
    determining a relative value of the pixel based on the current value and a reference value of the pixel measured without the presence of the transportable item.

15. The method of claim 14, wherein the directing further comprises:
    receiving microwave radiation at the transmit array from a microwave source; and
    reflecting the microwave radiation based on the respective programmed phase delays to direct the tansmit beam of microwave radiation toward the target.

16. The method of claim 15, wherein the receiving further comprises:
    receiving the receive beam from the target at the receive array; and
    reflecting the receive beam towards a receive microwave antenna based on the respective programmed phase delays.

17. The method of claim 14, wherein the measuring further comprises:
    determining the relative value of the pixel using scattering properties of the target when the target is spatially located near an edge of an imaging region defined between the transmit scanning panel and the receive scanning panel.

18. The method of claim 14, wherein the measuring further comprises:
   determining the relative value of the pixel using transmissive properties of the target when the target is spatially located near a center of an imaging region defined between the transmit scanning panel and the receive scanning panel.

19. The method of claim 14, further comprising:
scanning the transportable item by repeating the directing, the receiving and the measuring for each of a plurality of targets of the transportable item to construct the image of the transportable item.

20. The method of claim 19, wherein the scanning further comprises:
   scanning the transportable item while the transportable item is moving through an imaging region defined between the transmit scanning panel and the receive scanning panel.

* * * * *

UNITED STATES PATENT AND TRADEMARK OFFICE
CERTIFICATE OF CORRECTION

PATENT NO. : 7,183,963 B2  
APPLICATION NO. : 11/088831  
DATED : February 27, 2007  
INVENTOR(S) : Lee et al.

It is certified that error appears in the above-identified patent and that said Letters Patent is hereby corrected as shown below:

In column 14, line 51, in Claim 15, delete "tansmit" and insert -- transmit --, therefor.

Signed and Sealed this

Twenty-ninth Day of May, 2007

JON W. DUDAS  
*Director of the United States Patent and Trademark Office*